(12) United States Patent
Schemitsch et al.

(10) Patent No.: US 11,457,954 B2
(45) Date of Patent: Oct. 4, 2022

(54) STRUT PLATE AND CABLING SYSTEM

(71) Applicant: Stryker European Operations Holdings LLC, Kalamazoo, MI (US)

(72) Inventors: Emil Schemitsch, Thornhill (CA); Michael Mckee, Mississauga (CA)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 105 days.

(21) Appl. No.: 16/845,330

(22) Filed: Apr. 10, 2020

(65) Prior Publication Data

US 2020/0237407 A1 Jul. 30, 2020

Related U.S. Application Data

(63) Continuation of application No. 14/949,185, filed on Nov. 23, 2015, now abandoned.
(60) Provisional application No. 62/083,491, filed on Nov. 24, 2014.

(51) Int. Cl.
| | | |
|---|---|---|
| *A61B 17/68* | (2006.01) | |
| *A61B 17/80* | (2006.01) | |
| *A61B 17/82* | (2006.01) | |
| *A61B 17/86* | (2006.01) | |
| *A61B 17/00* | (2006.01) | |

(52) U.S. Cl.
CPC .......... *A61B 17/683* (2013.01); *A61B 17/80* (2013.01); *A61B 17/82* (2013.01); *A61B 17/864* (2013.01); *A61B 17/8625* (2013.01); *A61B 17/866* (2013.01); *A61B 2017/00004* (2013.01)

(58) Field of Classification Search
CPC ....... A61B 17/80; A61B 17/82; A61B 17/863; A61B 17/8625; A61B 17/864; A61B 17/842; A61B 2017/00004

USPC .............. 606/70–71, 280, 281–286, 298
See application file for complete search history.

(56) References Cited

U.S. PATENT DOCUMENTS

| | | | |
|---|---|---|---|
| 3,900,025 A | 8/1975 | Barnes, Jr. | |
| 4,743,256 A | 5/1988 | Brantigan | |
| 5,665,089 A * | 9/1997 | Dall ....................... | A61B 17/82 606/71 |

(Continued)

FOREIGN PATENT DOCUMENTS

| | | |
|---|---|---|
| JP | 07116241 | 5/1995 |
| WO | 9200046 A1 | 1/1992 |
| WO | 2006065774 A1 | 6/2006 |

OTHER PUBLICATIONS

Lam, K.H., Nieuwenhuis, P., Molenaar, I. et al. J Mater Sci: Mater Med (1994) 5: 181. <https://doi.org/10.1007/BF00121086> accessed on Aug. 22, 2019 (Year: 1994).*

(Continued)

*Primary Examiner* — Marcela I. Shirsat
(74) *Attorney, Agent, or Firm* — Lerner, David, Littenberg, Krumholz & Mentlik, LLP

(57) ABSTRACT

A bone plate assembly and method of utilizing same are disclosed. The assembly includes at least two plates affixed to the bone in two different locations. One of the plates includes a porous bone in-growth surface, and may be entirely porous. The assembly may further include at least one bone screw and cable for affixing the plates to the bone. In the method of use, the plates may be affixed by the screws and/or cables and the plate including the porous surface may be left in place after bone is allowed to grow therein.

12 Claims, 3 Drawing Sheets

(56) References Cited

U.S. PATENT DOCUMENTS

| | | | |
|---|---|---|---|
| 5,702,399 A | 12/1997 | Kilpela et al. | |
| 5,810,824 A | 9/1998 | Chan | |
| 5,993,452 A * | 11/1999 | Vandewalle | A61B 17/82 |
| | | | 606/103 |
| 7,537,664 B2 | 5/2009 | O'Neill et al. | |
| 7,731,718 B2 | 6/2010 | Schwammberger et al. | |
| 8,142,434 B2 | 3/2012 | Bluechel | |
| 8,147,861 B2 | 4/2012 | Jones et al. | |
| 8,172,884 B2 | 5/2012 | Bouman | |
| 9,055,984 B2 | 6/2015 | Albertson et al. | |
| 9,135,374 B2 | 9/2015 | Jones et al. | |
| 9,180,010 B2 | 11/2015 | Dong et al. | |
| 2003/0135212 A1 | 7/2003 | Y. Chow | |
| 2005/0240198 A1 * | 10/2005 | Albertson | A61B 17/823 |
| | | | 606/103 |
| 2006/0147332 A1 | 7/2006 | Jones et al. | |
| 2006/0264949 A1 | 11/2006 | Kohut et al. | |
| 2007/0142914 A1 | 6/2007 | Jones et al. | |
| 2008/0004709 A1 | 1/2008 | O'Neill et al. | |
| 2008/0269893 A1 * | 10/2008 | Bhatnagar | A61B 17/7266 |
| | | | 623/11.11 |
| 2009/0287215 A1 | 11/2009 | Fisher et al. | |
| 2010/0211113 A1 | 8/2010 | Olson et al. | |
| 2013/0030480 A1 | 1/2013 | Donate et al. | |
| 2013/0096559 A1 | 4/2013 | Katrana et al. | |
| 2014/0107710 A1 | 4/2014 | Forderer et al. | |

OTHER PUBLICATIONS

Chandler HP, Tigges RG. Instructional Course Lectures, The American Academy of Orthopaedic Surgeons—The Role of Allografts in the Treatment of Periprosthetic Femoral Fractures. JBJS. Sep. 1, 1997;79(9):1422-32.

Extended European Search Report for Application No. EP15003353 dated Mar. 31, 2016.

ImplanTec Schweiz GmbH, <http://www.implan-tec.ch/cerclage.html>, 3 pages, Copyright © 2013-2015.

Lam KH, Nieuwenhuis P, Molenaar I, Esselbrugge H, Feijen J, Dijkstra PJ, Schakenraad JM. Biodegradation of porous versus non-porous poly (L-lactic acid) films. Journal of Materials Science: Materials in Medicine. Apr. 1, 1994;5(4):181-9.

U.S. Appl. No. 62/035,074, filed Aug. 8, 2014.

* cited by examiner

STRUT PLATE AND CABLING SYSTEM

CROSS-REFERENCE TO RELATED APPLICATIONS

The present application is a divisional of U.S. patent application Ser. No. 14/949,185, filed Nov. 23, 2015, which claims the benefit of U.S. provisional patent application No. 62/083,491 filed Nov. 24, 2014, the disclosures of which are incorporated herein by reference.

BACKGROUND OF THE INVENTION

The present invention pertains to orthopedic bone plates, and in particular, orthopedic bone plates with bone in-growth capabilities.

A common method utilized in repairing fractures of bones includes affixing bone plates to the bone with screws. Generally, the plates are oriented so that portions thereof are placed on either side of the fracture and screws are placed through at least one bone screw hole of each bone plate portion. Depending upon the particular anatomical area of the fracture, different plate designs exist. For instance, plates designed for use on the distal and proximal portions of long bones such as the femur or tibia may include a shaft and a head, with screw holes extending through each.

One issue that is often faced by surgeons is the tendency of bone screws inserted through bone plates to back out of the bone plate and/or bone after implantation. Many different bone plate configurations have been designed to prevent such occurrences. For instance, it has been known for some time to thread portions of the bone screws to the plate holes to prevent the unwanted back out. Likewise, different secondary fixation elements (e.g., caps or the like) have been utilized in prior art plates.

Another issue faced by surgeons is often encountered in repairing perio-prosthetic fractures, which are fractures that occur around an implanted prosthesis (e.g., those utilized in total hip, total knee, or total shoulder arthroplasty). Because of the already implanted prosthesis, and the tendency of the fractures to be somewhat complicated, perio-prosthetic fractures are typically complex and difficult to treat with conventional methods. For instance, in placing screws through a bone plate, it can be difficult for a surgeon to both navigate around the already implanted prosthesis and capture each of the bone fragments of the fracture.

Therefore, there exists a need for a bone plate and cabling system capable of treating fractures such as perio-prosthetic fractures, as well as providing an alternative to bone screws which have a tendency to back out.

BRIEF SUMMARY OF THE INVENTION

A first aspect of the present invention is a bone plate assembly for fixing a fracture of a bone. The bone plate assembly includes a first bone plate attached to the bone and a second bone plate attached to the bone. The second bone plate includes a porous bone in-growth surface.

In one embodiment of the first aspect the first and second bone plates are attached to opposite sides of the bone. The assembly may further include at least one screw extending through the first bone plate and into the bone and at least one cable extending around the first and second plates. The at least one screw may be cannulated and the at least one cable may extend therethrough. The first plate may include a channel or slot and the at least one cable may extend through the channel or slot. The second bone plate may be entirely porous, or the bone in-growth surface may be attached to a solid portion. The first and second plates may be metallic, polymeric or any other suitable material.

A second aspect of the present invention is a method of fixing a fracture of a bone including the steps of attaching a first plate to the bone so that the first plate spans at least a portion of the fracture, attaching a second plate to the bone so that the second plate spans at least a portion of the fracture and allowing bone to grow into at least a portion of the second plate.

Other embodiments of the second aspect may further include the step of removing the first plate subsequent to the allowing step. The second plate may include a porous bone in-growth surface. The attaching the first plate step may include inserting at least one bone screw through the first plate and into the bone. The attaching steps may include wrapping at least one cable around the first and second plates. The cable may be placed through the at least one screw, a channel or slot or a cable plug.

BRIEF DESCRIPTION OF THE DRAWINGS

A more complete appreciation of the subject matter of the present invention and of the various advantages thereof can be realized by reference of the following detailed description in which references made to the accompanying drawings in which.

DETAILED DESCRIPTION

The present invention addresses both above-noted needs, by providing a bone plate and cabling system that does not rely solely upon bone screws inserted through the plate. Rather, the present invention makes use of porous plates that can be initially affixed via a novel cabling system and thereafter allow for bone ingrowth into the plates to support the construct. Although the porous bone plates disclosed herein are described as being constructed of porous metal foam, it is contemplated that the bone plates may be of many different types of materials, including, but limited, ceramics, plastics or the like. It is also contemplated to utilize the porous bone plates of the present invention in conjunction with more standard bone plates known in the art.

Figure 1:
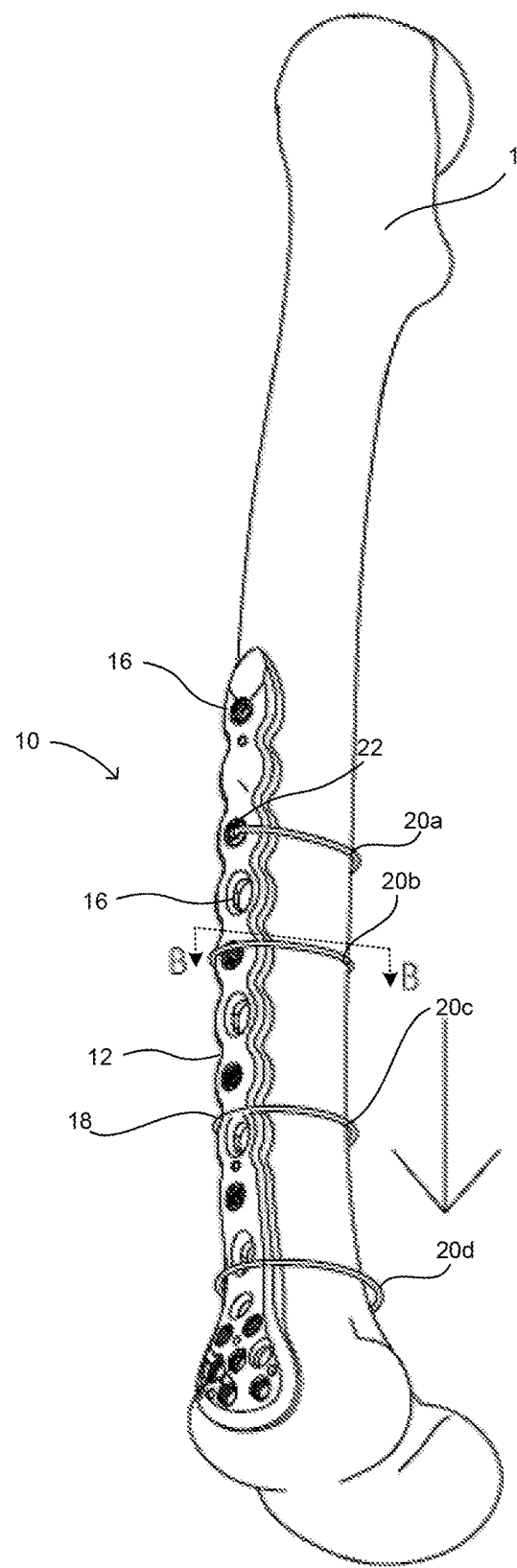
FIG. 1 is a perspective view of a bone plate and cabling system according to one embodiment of the present invention attached to a femur.
Figure 2:
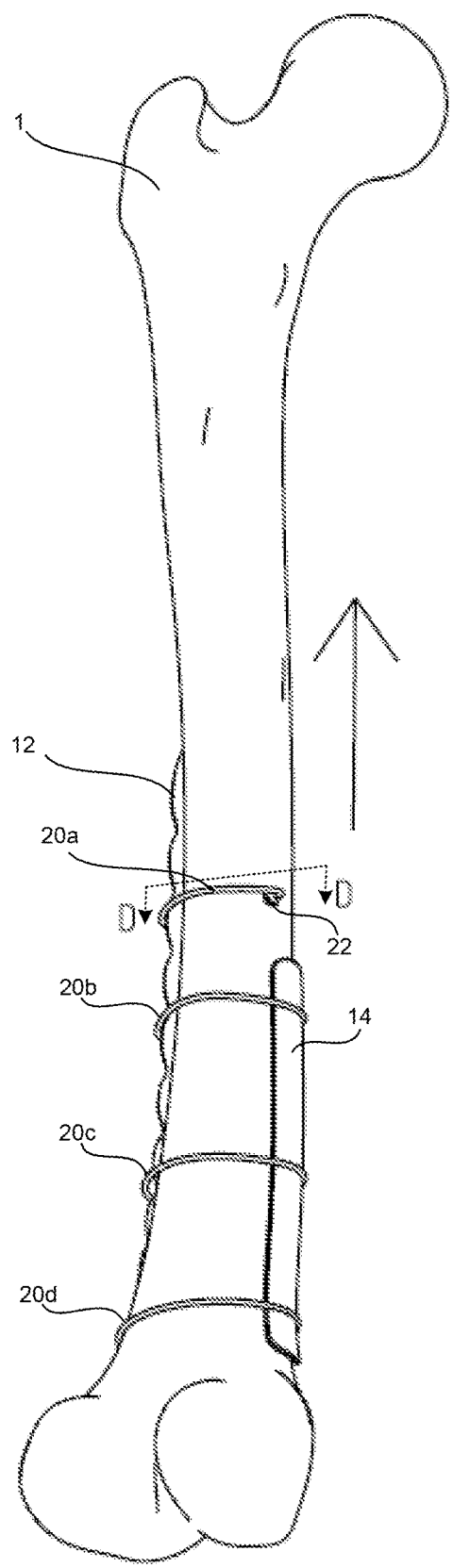
FIG. 2 is another perspective view of the bone plate and cabling construct of FIG. 1 focusing on a different plate of the construct.

FIGS. 1 and 2 depict a femur 1 with a bone plate and cabling system 10 attached thereto. System 10, as shown, includes a first bone plate 12 and a second bone plate 14 (best shown in FIG. 2). Bone plate 12 is standard bone with a plurality of bone plate holes 16 that are shown both as exhibiting circular and elongate forms. Of course, the holes may exhibit any shape or construct known in the art, including, without limitation, oblong compression holes, threaded holes and holes that include deformable structures. Likewise, any number of holes may be provided on plate 12 in connection with the present invention. Additionally, plate 12 includes at least one channel or slot 18 that is sized and shaped to accept and retain a cable of the type discussed more fully below. As shown, plate 12 is designed for use in connection with a distal femur, but can exhibit many different configurations depending upon the bone that requires repair.

On the other hand, bone plate 14 is shown constructed of porous material, with no holes formed therethrough. The porous material is preferably designed to allow for bone to grow directly into plate 14 after implantation. Although shown as consisting largely of the porous material, plate 14 can be only partially formed of the porous material. Specifically, in other embodiments, bone plate 14 may include an underside surface that is of a porous construction, so that when placed against the bone it can facilitate bone in-growth from the affected bone into the plate. In such a case, the remainder of the plate can be of a more solid construction.

As shown, the porous metallic construction of bone plate 14 was created utilizing a laser remelting process ("LRM"). In fact, it is contemplated to form the entirety of plate 14 with such a process, including any solid portions that may be included therein. Those solid portions could alternatively be formed through more conventional processes (e.g., molding, forging, etc. . . . ) and a porous lower or bone contacting surface can be later affixed thereto via a process like LRM. Without limitation, the LRM processes disclosed in U.S. Pat. Nos. 7,537,664 and 8,147,861; U.S. Patent Application Publications Nos. 2006/0147332, 2007/0142914, 2008/0004709; and U.S. patent application Ser. Nos. 13/441,154 and 13/618,218, the disclosures of which are hereby incorporated by reference herein, can be utilized. It is also contemplated to form any porous surface via a laser etching procedure.

Also depicted in FIGS. 1 and 2 is a cabling system that includes plurality of cables 20a-d and at least one cannulated screw 22. As shown, the cables may be situated so as to extend through screw 22 and around plate 12 and the femur (cable 20a), around both plates 12 and 14 (cables 20b and 20d) and through channel or slot 18 and around plate 14 (cable 20c). Of course, other configurations are also contemplated depending upon the bone being repaired and the plates being utilized.

Figure 3:
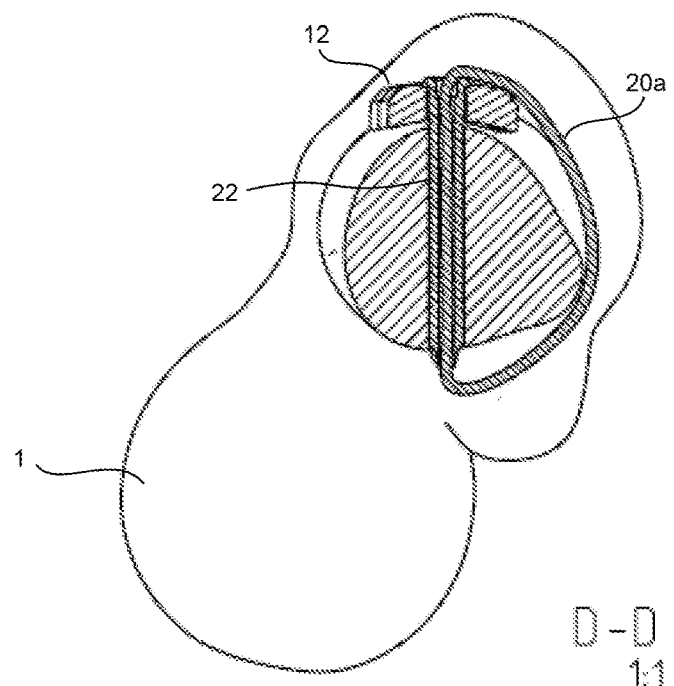
FIG. 3 is a cross sectional view taken along line D-D of FIG. 2.
Figure 4:
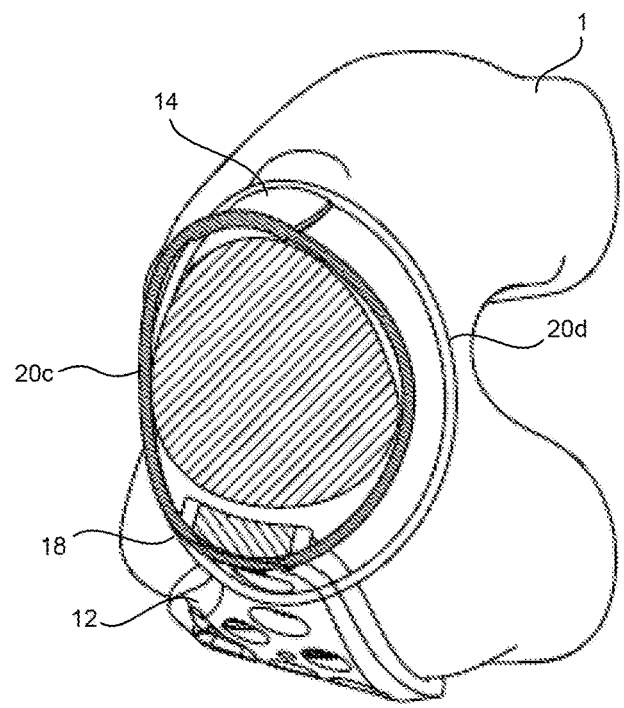
FIG. 4 is a cross sectional view taken along line B-B of FIG. 1.

Screw 22 not only allows for the fixation of plate 12 to the bone, but also its cannulation allows for passage of cable 20a therethrough so that the cable only needs to wrap around the affected bone on one side thereof. This is further shown in the cross sectional view of FIG. 3. Although screw 22 is shown as a one piece screw, it is contemplated that the screw can include a modular head or the like. In addition, it is contemplated for one or more of plate holes 16 to be designed such that they are not only sized and shaped to receive the screws, but also allow polyaxial movement of the screws with respect to the plate. Above-mentioned channel or slot 18 is sized, shaped and oriented to receive and guide a cable placed therethrough. The channel or slot 18 can be of an open or closed design, the latter of which entirely retains the cable therein. Of course, although only a single channel or slot is shown included on plate 12, any number of them may be provided on a given plate.

In use, a surgeon will place plate 12 against an affected bone (such as femur 1), so that different portions of the plate span any fracture(s) in the bone. Thereafter screws, such as screws 22, may be placed through the plate and into the bone. Cables 20a-d may then be applied to the construct and plate 14 may be introduced to the opposite side of the bone from plate 12. It is also contemplated to place plate 14 in other positions than directly opposite to plate 12 (e.g., to the side of the bone). Upon tightening of the cables, plates 12 and 14 are fixed in position.

In the case of a peri-prosthetic fracture, care must be taken as to the placement of any screws so as not to interfere with the already implanted prosthesis. However, it is possible through the use of the plates, screws and cables of the present invention properly stabilize the fracture without the need for screws extending into each bone fragment. Rather, less screws can be utilized when utilizing cables 26. The cables act to stabilize the fracture, much like multiple screws would in the case of a standard bone plate use. This is especially true in the context of peri-prosthetic fractures, where the amount of bone screws that can be utilized is limited.

In situations in which bone plates 12 and 14 are utilized, the use of two plates allows for a stable fixation of the bone fracture via plate 12, while bone is allowed to grow into plate 14. After proper bone growth, a surgeon may elect to remove bone plate 12 from the fracture site, thereby leaving what is effectively become a continuous bone/plate 14 construct. It is, of course, contemplated that the plates may be placed on many different portions of the bone, as well as to leave both plates in place for an extended period of time. Additionally, it is contemplated to utilize only plate 14 with one or more cables at least initially holding it in place. After proper bone growth into plate 14, the cables may be removed. It is to be understood that plate 14 could also be designed to work in conjunction with screws, like screw 22, or to include one or more channels or slots like are discussed above. Any holes provided in plates 12 or 14 could also accept a cable plug, which can provide an additional mechanism for associating the plate with a cable. For instance, it is envisioned to utilize with plates 12 or 14 any of the cables plugs disclosed in U.S. Pat. No. 8,142,434, U.S. Patent Application Publication No. 2014/0107710 and U.S. Provisional Application No. 62/035,074, the disclosures of which are hereby incorporated by reference herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of fixing a fracture of a bone comprising the steps of:
    placing a first plate on the bone such that the first plate spans at least a portion of the fracture;
    inserting at least one screw through the first plate and into the bone;
    placing a second plate on the bone such that the second plate spans at least a portion of the fracture, wherein the second plate is constructed entirely from porous metal foam; and
    attaching the second plate to the bone without the use of a screw, the second plate including a bone in-growth surface, an outward facing surface opposite the bone in-growth surface, and no holes extending between the bone in-growth surface and the outward facing surface and traversing the outward facing surface,
        wherein the attaching of the second plate includes wrapping at least one cable around the second plate such that the at least one cable is wrapped along the outward facing surface.

2. The method of claim 1, wherein wrapping the at least one cable includes inserting the at least one cable through a cannulation in the at least one screw.

3. The method of claim 1, wherein wrapping the at least one cable includes inserting the at least one cable through at least one channel in the first plate.

4. The method of claim 1, wherein attaching the second plate includes attaching the second plate opposite the first plate.

5. The method of claim 1, further comprising:
allowing bone to grow into at least a portion of the bone in-growth surface; and
removing the first plate or the at least one cable subsequent to the allowing step.

6. A method of fixing a fracture of a bone, the method comprising:
placing a first plate on the bone such that the first plate spans at least a portion of the fracture;
placing a second plate on the bone such that the second plate spans at least a portion of the fracture, the second plate including a bone in-growth portion, an outward facing surface opposite the bone in-growth portion, and no holes extend continuously between the bone in-growth portion and the outward facing surface and traversing the outward facing surface, wherein the second plate is constructed entirely from porous metal foam; and
wrapping at least one cable around the first and second plates to attach the first and second plates to the bone such that the at least one cable is wrapped along the outward facing surface of the second plate.

7. The method of claim 6, further comprising inserting at least one screw through the first plate and into the bone.

8. The method of claim 7, wherein wrapping the at least one cable includes inserting the at least one cable through a cannulation in the at least one screw.

9. The method of claim 6, wherein wrapping the at least one cable includes inserting at least one cable through at least one channel in the first plate.

10. The method of claim 6, wherein placing the second plate includes placing the second plate opposite the first plate.

11. The method of claim 6, further comprising:
allowing bone to grow into a least a portion of the bone in-growth portion; and
removing the first plate or the at least one cable subsequent to the allowing step.

12. A method of fixing a fracture of a bone, the method comprising:
placing a first plate on the bone such that the first plate spans at least a portion of the fracture, wherein the first plate includes a throughbore extending transverse to a longitudinal axis of the first plate;
inserting at least one cannulated screw through the first plate and into the bone;
placing a second plate on the bone such that the second plate spans at least a portion of the fracture, wherein the second plate is constructed entirely from porous metal foam;
inserting at least one cable through a cannulation in the at least one screw; and
wrapping the at least one cable around an outward facing surface of the first plate and an outward facing surface of the second plate,
wherein wrapping the at least one cable around the outward surface of the second plate attaches the second plate to the bone without the use of a screw, and
wherein wrapping the at least one cable further includes inserting the at least one cable through the throughbore.

* * * * *